(12) United States Patent
Snowden et al.

(10) Patent No.: US 9,151,754 B2
(45) Date of Patent: Oct. 6, 2015

(54) DIAGNOSTIC TEST DEVICE WITH IMPROVED STRUCTURE

(71) Applicant: CHURCH & DWIGHT CO., INC., Princeton, NJ (US)

(72) Inventors: Timothy Snowden, Howell, NJ (US); Kristen Buentello, Newtown, PA (US); Ashley Tomasello, Bordentown, NJ (US); Dean M. Mohamed, Clifton, NJ (US)

(73) Assignee: CHURCH & DWIGHT CO., INC., Princeton, NJ (US)

( * ) Notice: Subject to any disclaimer, the term of this patent is extended or adjusted under 35 U.S.C. 154(b) by 64 days.

(21) Appl. No.: 13/834,596

(22) Filed: Mar. 15, 2013

(65) Prior Publication Data

US 2014/0273012 A1    Sep. 18, 2014

(51) Int. Cl.
*G01N 33/558* (2006.01)
*A61B 10/00* (2006.01)
*G01N 33/543* (2006.01)

(52) U.S. Cl.
CPC ........... *G01N 33/558* (2013.01); *A61B 10/0045* (2013.01); *A61B 2560/0406* (2013.01); *A61B 2560/0425* (2013.01); *A61B 2560/0431* (2013.01); *G01N 33/54366* (2013.01)

(58) Field of Classification Search
USPC ......................................................... 422/401
See application file for complete search history.

(56) References Cited

U.S. PATENT DOCUMENTS

| | | |
|---|---|---|
| D348,735 S | 7/1994 | Groothuizen |
| D373,829 S | 9/1996 | Pallender |
| 5,602,040 A | 2/1997 | May et al. |
| 5,622,871 A | 4/1997 | May et al. |
| 5,656,503 A | 8/1997 | May et al. |
| D383,549 S | 9/1997 | Arnett et al. |

(Continued)

FOREIGN PATENT DOCUMENTS

WO    9009592    8/1990

OTHER PUBLICATIONS

"Clearblue® PLUS Pregnancy Test." http://www.clearblueeasy.com/clearblue-plus-pregnancy-test.php Swiss Precision Diagnostics GmbH, n.d. Web. Jan. 16, 2013. http://www.clearblueeasy.com/clearblue-plus-pregnancy-test.php.

(Continued)

*Primary Examiner* — Melanie Y Brown
*Assistant Examiner* — Rebecca Martinez
(74) *Attorney, Agent, or Firm* — Ryan Cagle; Womble, Carlyle, Sandridge & Rice LLP

(57) ABSTRACT

The present disclosure relates to diagnostic test devices that provide increased comfort and ease of use. The diagnostic test device can include a test member, such as a lateral flow assay test strip. The test device can further comprise a housing that comprises a substantially arch shaped handle. The housing of the test device can comprise a base member that is attached to a curved lower surface of the housing and that can improve stability of the device in an upward facing position as well as enable angled positioning of the device relative to a flat, horizontal surface. The curvature of the test device in particular can provide secure handling of the device while also improving ease and comfort of use thereof. The disclosure further relates to methods of determining the presence of an analyte in a fluid sample and methods for evaluating a test result of a personal use diagnostic test device.

41 Claims, 14 Drawing Sheets

(56) References Cited

U.S. PATENT DOCUMENTS

| | | | |
|---|---|---|---|
| 5,714,389 A | 2/1998 | Charlton et al. | |
| 5,739,041 A | 4/1998 | Nazareth et al. | |
| 5,846,835 A | 12/1998 | Sisbarro et al. | |
| 6,046,057 A | 4/2000 | Nazareth et al. | |
| 6,187,598 B1 | 2/2001 | May et al. | |
| 6,228,660 B1 | 5/2001 | May et al. | |
| 6,277,650 B1 | 8/2001 | Nazareth et al. | |
| 6,319,676 B1 | 11/2001 | Nazareth et al. | |
| 6,352,862 B1 | 3/2002 | Davis et al. | |
| 6,485,982 B1 | 11/2002 | Charlton | |
| D491,274 S | 6/2004 | Dubniczki et al. | |
| 6,767,714 B2 | 7/2004 | Nazareth et al. | |
| D499,812 S | 12/2004 | Wu | |
| D509,901 S | 9/2005 | Phelan et al. | |
| D511,574 S | 11/2005 | Wendling | |
| D512,156 S | 11/2005 | Wendling | |
| 7,045,342 B2 | 5/2006 | Nazareth et al. | |
| D523,964 S | 6/2006 | Phelan et al. | |
| D530,825 S | 10/2006 | Lee et al. | |
| D531,735 S | 11/2006 | Lee et al. | |
| D536,798 S | 2/2007 | Lee et al. | |
| D537,167 S | 2/2007 | Sigel et al. | |
| D537,168 S | 2/2007 | Sigel et al. | |
| D537,169 S | 2/2007 | Sigel et al. | |
| D537,531 S | 2/2007 | Sigel et al. | |
| 7,214,542 B2 | 5/2007 | Hutchinson | |
| 7,220,597 B2 | 5/2007 | Zin et al. | |
| 7,238,537 B2 | 7/2007 | Davis et al. | |
| D548,359 S | 8/2007 | Illein et al. | |
| D548,854 S | 8/2007 | Wendling | |
| D554,765 S | 11/2007 | Wendling | |
| D557,815 S | 12/2007 | Lee et al. | |
| 7,317,532 B2 | 1/2008 | Sharrock et al. | |
| D570,490 S | 6/2008 | Laverack | |
| D571,019 S | 6/2008 | Laverack | |
| D571,020 S | 6/2008 | Laverack | |
| 7,384,796 B2 | 6/2008 | Davis et al. | |
| D574,966 S | 8/2008 | Laverack | |
| D575,876 S | 8/2008 | Laverack | |
| D575,877 S | 8/2008 | Laverack | |
| 7,407,813 B2 | 8/2008 | Davis et al. | |
| D576,737 S | 9/2008 | Lee et al. | |
| 7,432,111 B2 | 10/2008 | Cho et al. | |
| 7,499,170 B2 | 3/2009 | Sasaki et al. | |
| D592,759 S | 5/2009 | Laverack | |
| 7,632,687 B2 | 12/2009 | Gokhan | |
| 7,763,454 B2 | 7/2010 | Nazareth et al. | |
| 7,776,618 B2 | 8/2010 | Nazareth et al. | |
| D627,882 S | 11/2010 | Slowey et al. | |
| D655,424 S | 3/2012 | Castanon et al. | |
| 8,211,711 B2 | 7/2012 | Nazareth et al. | |
| 8,268,636 B2 | 9/2012 | Nazareth et al. | |
| D672,880 S | 12/2012 | Laverack et al. | |
| D673,265 S | 12/2012 | Nonnemacher et al. | |
| D676,144 S | 2/2013 | Laverack et al. | |
| D676,569 S | 2/2013 | Laverack et al. | |
| 2001/0051350 A1 | 12/2001 | Nazareth | |
| 2002/0042082 A1 | 4/2002 | Nazareth et al. | |
| 2004/0171174 A1 | 9/2004 | Nazareth et al. | |
| 2008/0124244 A1 | 5/2008 | Sigel et al. | |
| 2008/0131317 A1 | 6/2008 | Davis et al. | |
| 2008/0213920 A1 | 9/2008 | Nazareth et al. | |
| 2009/0117665 A1* | 5/2009 | Tung et al. | 436/501 |
| 2009/0208371 A1 | 8/2009 | Hannat et al. | |
| 2010/0137741 A1 | 6/2010 | Slowey et al. | |
| 2010/0239460 A1 | 9/2010 | Nazareth et al. | |
| 2010/0240149 A1 | 9/2010 | Nazareth et al. | |
| 2010/0255609 A1* | 10/2010 | Rutter et al. | 436/518 |
| 2010/0261293 A1 | 10/2010 | Nazareth et al. | |
| 2010/0267166 A1 | 10/2010 | Nazareth et al. | |
| 2011/0201122 A1 | 8/2011 | Nazareth et al. | |
| 2012/0072125 A1 | 3/2012 | Sharrock | |
| 2012/0082597 A1* | 4/2012 | Doniger et al. | 422/401 |
| 2012/0083044 A1 | 4/2012 | Sturman et al. | |
| 2013/0065321 A1 | 3/2013 | Nazareth et al. | |

OTHER PUBLICATIONS

"Clearblue® PLUS Pregnancy Test" Leaflet. http://www.clearblueeasy.com/clearblue-plus-pregnancy-test.php Swiss Precision Diagnostics GmbH, Aug. 2011. Web. Jan. 16, 2013.

International Search Report for PCT/US2014/018539 mailed Jun. 2, 2014, which pertains to this subject application.

* cited by examiner

DIAGNOSTIC TEST DEVICE WITH IMPROVED STRUCTURE

FIELD OF THE DISCLOSURE

The present disclosure relates to diagnostic test devices that provide increased ease of use. More particularly, the test devices include structural and functional elements that improve user handling and evaluation of the device.

BACKGROUND

Many types of ligand-receptor assays have been used to detect the presence of various substances in body fluids, such as urine, saliva, or blood. Some commercially available assays are designed to make a quantitative determination, but in many circumstances all that is required is a qualitative positive/negative indication. Examples of such qualitative assays include blood typing, pregnancy testing, and many types of urinalysis.

U.S. Pat. No. 6,485,982, which is incorporated herein by reference in its entirety, describes a diagnostic test cell or device formed of an elongated outer casing which houses an interior permeable material (such as glass fiber) capable of transporting an aqueous solution by capillary action, wicking, or simple wetting. The casing defines a sample inlet, and interior regions, which are designated as a test volume and a reservoir volume. The reservoir volume is disposed in a section of the test cell spaced apart from the inlet and is filled with sorbent material. The reservoir acts to receive a fluid sample transported along a flow path defined by the permeable material and extending from the inlet and through the test volume. In the test volume is a test site comprising a first protein having a binding site specific to a first epitope of the ligand immobilized in fluid communication with the flow path (e.g., bound to the permeable material or to latex particles entrapped in or bonded to the permeable material). A window, such as a hole or transparent section of the casing, permits observations of the test site through the casing wall. The use of the test cell requires a conjugate comprising a second protein bound to colored particles, such as a metal sol or colloid, preferably gold. The conjugate can take two distinct forms, depending on whether the assay is designed to exploit the "sandwich" or "competitive" technique.

U.S. Pat. No. 7,045,342, which is incorporated herein by reference in its entirety, describes a diagnostic test device including a biphasic chromatographic medium. The biphasic substrate is formed of a release medium joined to a capture medium located downstream of the release medium. The release and capture media preferably comprise two different materials, or phases, having different specific characteristics. The two phases are joined together to form a single fluid path such that a solvent front can travel unimpeded from the proximal (upstream) end of the release medium to the distal (downstream) end of the capture medium.

For tests such as those described above, visually observable indicia can be preferred. Such indicia typically have included the presence of agglutination or a color change at a defined site on the assay. More recent efforts have included providing electronic (i.e., digital) signals as the observable indicia. For example, U.S. Pat. No. 7,763,454, which is incorporated herein by reference in its entirety, describes an electronic analyte assaying device that includes an electronic processing system and a liquid crystal display (LCD). The device includes a chromatographic medium and utilizes electronic components for evaluation of the test as well as display of the test results. Nevertheless, user interface with diagnostic test devices remain limited.

In particular, known point of care or over the counter diagnostic test devices lack an ergonomically favorable structure. As such, it is often difficult for a user to handle the device during application of the test fluid, such as from a urine stream, which can lead to either insufficient fluid application or device flooding. Because of these and other reasons, it would be beneficial to provide a personal use test device with improved ergonomic structure for ease of grip and use.

SUMMARY OF THE DISCLOSURE

The present disclosure relates to diagnostic test devices that include elements useful for carrying out an assay and for providing information related to the assay in an informative display. As an illustrative example, a pregnancy test device can be provided and can include elements for carrying out a test on a fluid sample applied to a receiving member so as to identify the presence of human chorionic gonadotropin (hCG) in the sample that is indicative of a pregnancy status. The diagnostic test devices are adapted to provide improved ergonomics and ease of use of the devices in various methods.

In one aspect, the present disclosure relates to a diagnostic test device. The device can comprise a lateral flow test component that is positioned inside a housing. Unlike known personal care test devices that are substantially straight, the presently disclosed test devices comprise a housing that is curved. In particular, the housing can include a substantially arch shaped handle. Further, the housing can comprise a housing body that is interconnected with the housing handle. The handle in some embodiments can be positioned so as to be entirely above the lower surface of the housing body.

Preferably, the diagnostic test device also comprises a base member that can be attached to a curved lower surface of the housing. The base member specifically can comprise a horizontal support surface. In some embodiments, the horizontal support surface can be substantially collinear with a lower surface of the housing body. Further, the base member can extend rearward from the lower surface of the housing body and can increase in height moving rearward. Beneficially, the horizontal support surface of the base member can effectively increase a support length of the lower surface of the housing body by about 5% or greater. Such support length can define the portion of the housing body that is in physical, supporting contact with a substantially flat, horizontal surface when the device is in an upward facing position. In some embodiments, the horizontal support surface of the base member can form an angle α with the curved lower surface of the housing. The value of the angle α can be, for example, about 5° or greater and, more particularly, can be about 5° to about 45°. The horizontal support surface of the base member can have a length of about 10 mm or greater or, more particularly, a length of about 10 mm to about 30 mm. In preferred embodiments, the base member can be monolithically formed with the housing. In some embodiments, the base member can be a single, unitary member. In other embodiments, the base member can be defined by a first base member wall and a second base member wall. Specifically, the base member walls can be curved. For example, the curved base member walls can be defined by a forward section and a rearward section, and the curved base member walls each can comprise a convex curve in the forward sections thereof and a concave curve in the rearward sections thereof with respect to outer surfaces of the walls. More particularly, the curved base member walls can define a width $W_{BM1}$ at the forward section thereof, a width $W_{BM2}$ at a central section thereof, and a width $W_{BM3}$ at the rearward section thereof. In some embodiments, the respective widths can be defined by the formula $W_{BM1}<W_{BM2}>W_{BM3}$.

In certain embodiments, the housing body can be defined by a lower housing body and an upper housing body. The lower housing body can comprise a sidewall that is defined by an angle relative to a lower surface of the lower housing body. As an example, the angle can be greater than 0° and less than 90°. Similarly, the upper housing body can comprise a sidewall that is defined by an angle relative to an upper surface of the upper housing body. The angle also can be greater than 0° and less than 90°.

In some embodiments, the substantially arch shaped handle can be defined by an ascending section, a transverse section, and a descending section. Further, the handle can be defined by a total height $h_1$ that is a distance between an apex of an upper surface of the transverse section of the handle and a lower surface of the housing body, the height $h_1$ being about 15 mm or greater and more particularly about 15 mm to about 40 mm. The handle also can have a thickness $T_{handle}$ that can be, for example, about 6 mm to about 18 mm. The handle further can be defined by a partial height $h_2$ that is a distance between the apex of the upper surface of the transverse section of the handle and a bottom of a terminus of the handle, and $h_2$ can be defined by the formula $h_1>h_2>T_{handle}$.

In further embodiments, the substantially arch shaped handle can comprise a concavity (i.e., a thumb grip recess) on an upper surface thereof. The concavity can be defined specifically on the upper surface of the descending section of the handle. The handle also can comprise textures on a lower surface thereof. For instance, the textures can be defined by a plurality of raised members and can comprise, for example, rubber or a further elastomeric material.

The diagnostic test device according to the present disclosure can have a length that can be greater than similar devices in the field. For example, the housing in combination with a cap can have an overall length of about 14 to about 20 cm. In certain embodiments, the housing handle can comprise a significant proportion of the overall length of the housing. For example, the handle can comprise about 30% or greater, preferably about 40% or greater, of the total length of the housing.

The diagnostic test device according to the present disclosure can comprise additional elements as well. For example, in some embodiments, the housing further comprises a housing midsection interconnecting the housing body and the housing handle. Additionally, the housing further can comprise a display window. As noted above, the device also can comprise a cap that removably engages the housing, particularly at a forward end of the housing body, and can cover a sample receiving member extending outward from the housing body.

The diagnostic test device according to the present disclosure particularly can be characterized by the nature of the sample receiving member extending outward from the housing at a forward end thereof. For example, the sample receiving member can have a surface area of about 15 cm² or greater, particularly about 15 cm² to about 25 cm². The sample receiving member also can be defined by a thickness of about 1.5 mm to about 2.4 mm, a width of about 16 mm to about 20 mm, and a length of about 45 mm to about 55 mm.

The lateral flow test component provided in the housing of the diagnostic test device can comprise particular elements. In particular, the lateral flow test component can comprise a biphasic substrate or a triphasic substrate. The lateral flow test component similarly can comprise a release medium in fluid communication with a capture medium. Specifically, the release medium can comprise one or more releasably attached antibodies that are reactive with an analyte. In particular embodiments, the analyte can be selected from the group consisting of human chorionic gonadotropin (hCG), luteinizing hormone (LH), follicle stimulating hormone (FSH), thyroid stimulating hormone, estrogen, progesterone, testosterone, a metabolite thereof, and combinations thereof.

In another aspect, the present disclosure also can relate to a method for determining the presence of an analyte in a fluid sample. In some embodiments, the method can comprise the following steps: providing a diagnostic test device comprising a lateral flow test component positioned inside a housing that includes a substantially arch shaped handle and a display window, the lateral flow test component comprising a sample receiving member and one or more substrates adapted for release and capture of one or more antibodies; applying a fluid sample to the sample receiving member; and observing a test result in the display window, the test result being indicative of the presence of the analyte in the liquid sample.

In yet another aspect, the present disclosure can relate to a method for evaluating a test result of a personal use diagnostic test device. In some embodiments, the method can comprise the following steps: carrying out a test with a diagnostic test device comprising a lateral flow test component positioned inside a housing that comprises a housing body interconnected with a substantially arch shaped handle, a display window on an upper surface of the housing by which the test result is visible, and a base member attached to a curved lower surface of the housing; positioning the diagnostic test device at an angle relative to a substantially flat, horizontal surface such that the diagnostic test device is self-maintained at the angle. The diagnostic test device may incorporate a variety of structural components that facilitate self-maintenance of the angled positioning. In one embodiment, the self-maintenance means can be defined by a three point contact with the substantially flat, horizontal surface; and viewing the visible test result in the display window. In particular embodiments, the three point contact can be defined by contact between the substantially flat, horizontal surface and each of a wall of the base member, a side wall of the housing body, and a side wall of the handle. More particularly, the substantially arch shaped handle can be defined by an ascending section and a descending section, and the side wall of the handle defining one of the three point contacts can be in the descending section thereof. In specific embodiments, the angle of the device relative to the substantially flat, horizontal surface can be greater than 0° and less than 90°, more particularly about 10° to about 85°.

BRIEF DESCRIPTION OF THE DRAWINGS

The present disclosure is particularly described in reference to the following figures; however, such figures are provided to illustrate only preferred embodiments of the disclosure, and the disclosure is not intended to be limited thereto.

DETAILED DESCRIPTION OF THE DISCLOSURE

Figure 1:
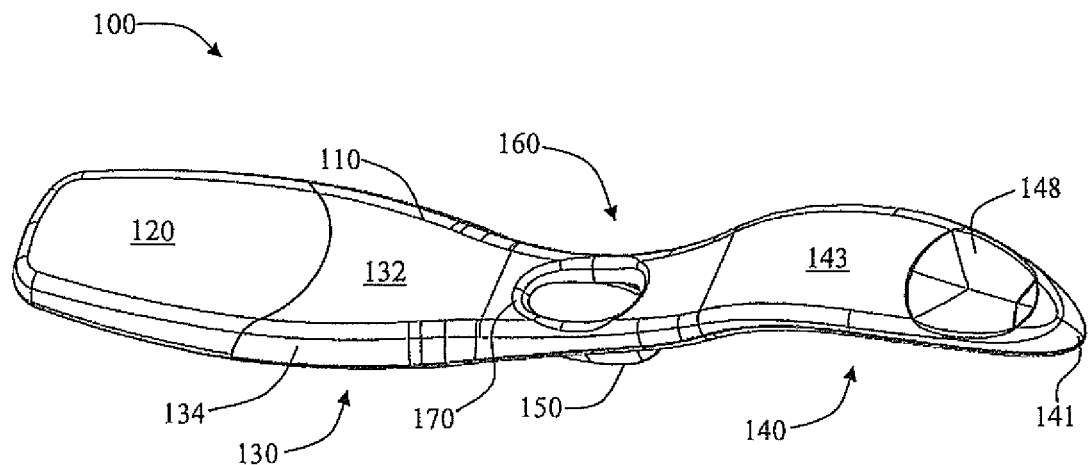
FIG. 1 is a top perspective view of a diagnostic test device according to an example embodiment of the present disclosure illustrating a curved housing defining the outer surfaces of the device.

The present disclosure now will be described more fully hereinafter with reference to specific embodiments and particularly to the various drawings provided herewith. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

In one aspect, the present disclosure relates to a test device, such as an over-the-counter (OTC), personal use, or point of care (POC) test device, for detecting an analyte in a sample. The device generally includes components suitable for carrying out an assay, such as a lateral flow assay, and also includes components suitable for communicating information relating to the assay to an individual. The test components can be contained in a housing that is structured so as to provide improved ease of use of the test device.

The test components in a broad sense can comprise a proximal portion (e.g., a sample receiving member) in fluid communication with a distal portion (e.g., a reservoir). The proximal and distal portions may be interconnected by a substrate material, which itself may form all or part of the proximal and/or distal portion of the device. A sample (e.g., urine) can be directly or indirectly applied to the proximal portion of the device for transport to the distal portion. Preferably, the sample flows across the substrate so as to contact one or more antibodies attached to or otherwise deposited on the substrate. The antibodies can be designed and/or chosen to recognize a variety of analytes. In specific embodiments, a test device according to the present disclosure can be useful for detection of human chorionic gonadotropin (hCG), luteinizing hormone (LH), follicle stimulating hormone (FSH), thyroid stimulating hormone, estrogen, progesterone, testosterone, a metabolite thereof, and combinations thereof. Even further analytes also can be encompassed by the present disclosure.

The devices disclosed herein can make use of a variety of techniques for detecting the presence of an analyte. One example is a sandwich technique wherein one or more antibodies used in the detection comprise a binding member or site which binds to an epitope on the analyte for detection. A labeled antibody binds to the analyte to form a complex in the sample. The analyte, which is bound to the labeled antibody or antibodies, binds with one or more capture antibodies to form a "sandwich," comprising the capture antibody, analyte (or antigen), and the labeled antibody. Each sandwich complex thus produced comprises three components: one capture antibody, one antigen, and one labeled antibody. An antibody used herein can be a polypeptide substantially encoded by an immunoglobulin gene or immunoglobulin genes, or fragments thereof, which may specifically recognize and bind an antigen. The recognized immunoglobulin genes include the kappa, lambda, alpha, gamma, delta, epsilon, and mu constant region genes, as well as the immunoglobulin variable region genes. Antibodies include fragments, such as Fab', F(ab)$_2$, Fabc, and Fv fragments. The teem antibody also can include antibody fragments either produced by the modification of whole antibodies or those synthesized de novo using recombinant DNA methodologies, and further can include "humanized" antibodies made by conventional techniques. Although polyclonal antibodies can be used, antibodies are preferably monoclonal antibodies. A capture antibody according to the disclosure can be an antibody attached to a substrate directly or indirectly, such as a solid substrate. The capture antibody can include at least one binding member that specifically or preferentially binds a particular distinct epitope of an antigen.

In the sandwich technique, the makeup of each sandwich complex can vary depending upon the particular labeled antibody (and thus the particular antigen) included therein. In the same test, there can be multiple different types of sandwiches produced. The sandwich complexes are progressively produced as the test sample with the analyte therein continuously moves along the substrate of the device. As more and more of the analyte/labeled antibody complex is immobilized in sandwich form with the capture antibody or antibodies at the capture site, the label components aggregate and become detectable in that the accumulation of the sandwich complexes at the capture site can be detected in various ways, such as by visual inspection of, for example, color development at the capture site or by a digital readout resulting from the electronic analysis of the aggregate at the capture site as further described herein. Although the sandwich technique is provided as an exemplary embodiment, the devices described herein in relation to the improved communication aspects are not limited to such underlying technique. Rather, other techniques for identifying an analyte in a test sample and forming a detectable signal based on the presence or absence of the analyte in the sample can be utilized.

Exemplary means for forming a detectable signal can comprise the use of a conjugate comprising one or more antibodies bound to detectable label components (e.g., colored particles, such as a metal sol or colloid particles). One or more of the antibodies used in the disclosed devices (e.g., one or two) can be labeled. Any detectable label recognized in the art as being useful in various assays can be used. In particular, the detectable label component can include compositions detectable by reflective, spectroscopic, photochemical, biochemical, immunochemical, or chemical means. As such, the label component produces a detectable signal. For instance, suitable labels include soluble dyes, fluorescent dyes, chemiluminescent compounds, radioisotopes, electron-dense reagents, enzymes, colored particles, or dioxigenin. The label component can generate a measurable signal, such as radioactivity, fluorescent light, color, or enzyme activity, which can be used to identify and quantify the amount of label bound to a capture site. Thus, the label component can also represent the presence or absence of a particular antigen bound thereto, as well as a relative amount of the antigen (e.g., relative to a known standard, threshold standard, or a different standard). The labeled materials can be detected through use of suitable electronic components, including hardware and software, and thus can be communicated to a user via digital signal or similar means. Further detail regarding the production of digital signals in personal use assays is provided, for example, in U.S. Pat. No. 7,214,542 to Hutchinson; U.S. Pat. No. 7,220,597 to Zin et al.; and U.S. Pat. No. 7,499,170 to Sasaki et al., which are incorporated herein by reference.

Devices according to the present disclosure can include one or more standards or internal controls that allow for determination of whether signal development is a true indication of the presence or absence of analyte in the sample or is simply an artifact, such as caused by nonspecific sorption. For example, a negative control site can be prepared identically to the test site, except that immobilization of the capture antibody is omitted. Therefore, although the conjugate will reach the negative control site, it will aggregate due only to non-specific binding. Similarly, the device can include a positive control, such as with an authentic sample of the analyte for detection immobilized at the positive control site. An alternate control site can be located downstream of the capture site and have immobilized thereon at least one capture antibody (e.g., a protein). Such control site can function to capture and immobilize labeled antibody which has not been captured at the capture site. For example, such control site can include polyclonal antisera specific for the labeled antibody immobilized thereon to indicate proper functioning of the assay.

In some embodiments, a biphasic chromatographic medium (substrate/test strip) can be used in the disclosed assays and can comprise an upstream release medium joined to a downstream capture medium. The release and capture media can comprise two different materials or phases having different specific characteristics. The two phases can be joined together to form a single fluid path such that a solvent front can travel unimpeded from the proximal (upstream) end of the release medium (which can be defined as a proximal portion of the biphasic medium) to the distal (downstream) end of the capture medium (which can be defined as a distal portion of the biphasic medium). A sample receiving member can be generally provided at the proximal end of the biphasic substrate and a reservoir of sorbent material can be located beyond the biphasic substrate.

In other embodiments, a triphasic chromatographic medium (substrate/test strip) can be used in the disclosed assays and can comprise a capture medium overlapped at one end by a release medium and at the opposing end by a reservoir. The triphasic substrate can be in fluid communication with a sample receiving member at the end thereof comprising the release medium.

In certain embodiments, use of a biphasic or triphasic chromatographic medium may enhance the speed and sensitivity of an assay, such as those described in U.S. Pat. Nos. 6,319,676, 6,767,714, 7,045,342, and U.S. Publication No. 2012/0083044, which are incorporated herein by reference, including without limitation for the purpose of describing biphasic and triphasic chromatographic media. Methods for manufacturing chromatographic media are also described in detail in U.S. Pat. No. 5,846,835, the disclosure of which is incorporated herein by reference in its entirety.

Reagents for detecting, labeling, and capturing an analyte of interest can be disposed on the release and capture media. In certain embodiments, one or more labeled conjugates can be located on the release medium and each can include a binding member (e.g., antibody) that may be reactive with a particular site (sometimes referred to as a "first epitope," "second epitope," etc.) on the analyte of interest. The labeled conjugates further can comprise one or more detectable markers (or labels), as discussed herein.

The release medium can be formed from a substance which allows for release of reagents deposited thereon, which can comprise reagents that are releasably (i.e., not permanently) bound to the release medium. The primary function of the release medium is first to support and to subsequently release and transport various immunological components of the assay, such as a labeled conjugate and/or a capturable conjugate, both of which are capable of binding to the analyte of interest. The release medium can be formed of any material capable of holding, releasing, and transporting various immunological parts of the test such as the labeled test component (e.g., a bibulous, hydrophilic material).

The capture medium can be formed from a material which permits immobilization of reagents for detection of the presence of analyte in the test fluid. Immobilization can refer to any interaction that results in antibodies or analytes being irreversibly bound to the substrate such that they are not appreciably washed away, e.g., during the course of a single use of the device. The capture medium can comprise hydrophilic polymeric materials, such as microporous films or membranes, which permit protein reagents to be immobilized directly on the membrane by passive adsorption without the need for chemical or physical fixation, although fixation as such is not excluded.

The release medium and capture medium can be joined via any suitable means. For example, the two media can be joined by overlapping the downstream edge of the release medium over the upstream edge of the capture medium. The various media components of the biphasic or triphasic substrate can be adhered to a clear polymer film or opaque sheet, thereby holding the media in place. Alternately, the media can be connected by a non-overlapping butt joint and may still be attached to an underlying support.

The diffusible and non-diffusible reagents can be applied to the release and capture media, respectively, by any suitable technique. In one embodiment, the diffusible antibody reagents can be applied to the release medium by direct application onto the surface of the medium and dried to form a band. Generally, reagents can be immobilized using absorption, adsorption, or ionic or covalent coupling, in accordance with any suitable methods.

In various embodiments, test devices according to the present disclosure can be adapted for improved ease of use of the device by a user. In particular, the disclosed test devices can comprise a housing that defines an ergonomically structured test device having test components housed therein. This contrasts with known POC and OTC diagnostic test devices that are typically defined by a housing that is straight, relatively short, and substantially flat. Such structure of known test devices can be difficult for a user to manipulate in a manner that reliably leads to proper test conditions to achieve the most accurate test results. For example, with test devices that detect an analyte in a urine sample, it can be beneficial to utilize midstream application of the urine to a sample applicator. The shapes and dimensions of typical, known test devices can make such devices difficult to use with midstream application. In particular, it can be difficult to ensure that enough sample is applied to achieve a complete and accurate test while also avoiding flooding of the test device by applying too much sample. Known test designs lend themselves for being held between the index finger and thumb (i.e., a "pinch" grip). The contouring provided according to the present disclosure, however, enables handling by multiple fingers and the thumb and thus provides the user with improved control of the device. Further, known test devices, because of their shape, provide for only a single positioning (i.e., flat) of the device such that the results of the test are viewable. Test devices according to the present disclosure overcome these shortfalls of the known devices.

In certain embodiments, a test device according to the present disclosure can comprise a housing with one or more curvatures defined therein. The housing particularly can be curved in two separate planes. The housing likewise can be curved in two, three, or more directions. The housing can be formed of two or more parts having interfitting parts that can be made of moisture impervious solid materials, for example, a plastic material. In other embodiments, a single part with a molded shape (e.g., a butterfly hinge) may be used. Non-limiting examples of commercially available plastics that can be used in forming the housing include polyvinyl chloride, polypropylene, polystyrene, polyethylene, polycarbonates, polysulfanes, polyesters, urethanes, epoxies, or other suitable materials. In some embodiments, if desired, the housing can be formed of one or more parts that are biodegradable, such as paper (optionally with a substantially water resistant coating, such as a wax) or biodegradable plastics, such as polylactic acid. The housing can be prepared by conventional methodologies, for example, standard molding technologies well known in the art. Such molding technologies can include, but are not limited to, injection molding, compression molding, transfer molding, blow molding, extrusion molding, foam molding, and thermoform molding. The aforementioned molding technologies are known in the art, and as such are not discussed in detail herein. See for example, Processes and Materials of Manufacture, Third Edition, R. A. Lindsberg (1983) Allyn and Baron pp. 393-431.

With reference to FIG. 1, an exemplary embodiment of a test device 100 according to the present disclosure can comprise a housing 110. The housing specifically can be defined by an upper housing 112 and a lower housing 114 (see FIG. 3) that are combined as discussed above. The housing comprises a housing body 130 that is interconnected with a housing handle 140 directly or through, for example, a housing midsection 160. The housing 110 further comprises a base member 150 that can provide a plurality of functions in balancing the test device 100 and aiding in positioning of the test device for evaluation. The test device further includes a cap 120 that removably engages the housing 110 so as to cover a sample receiving member.

Disposed within the housing 110 are the functional components forming a test member. The test member can be a single strip or a combination of strips of materials useful for providing an assay. For example, the test member can be a test strip as described herein, such as comprising a biphasic or triphasic substrate, for use in an assay. A sample receiving member 12 can be disposed within the housing, extend to the exterior thereof, and can be covered by the removable cap 120. The sample receiving member can have a surface area of about 15 $cm^2$ or greater, about 18 $cm^2$ or greater, or about 20 $cm^2$ or greater. In particular embodiments, the sample receiving member can have a surface area of about 15 $cm^2$ to about 25 $cm^2$, about 17 $cm^2$ to about 23 $cm^2$, or about 18 $cm^2$ to about 22 $cm^2$. In specific embodiments, the sample receiving member can have the following dimensions: thickness—about 1.5 mm to about 2.4 mm or about 1.7 mm to about 2.1 mm; width—about 16 mm to about 20 mm or about 17 mm to about 19 mm; length—about 45 mm to about 55 mm or about 47 mm to about 53 mm.

In use, a test subject applies a test sample to a sample receiving member 12. The test sample then passes from the sample receiving member 12 to a test member, such as a chromatographic substrate, where the sample is in reactive contact with the test site (e.g., the capture site), and optionally one or more control sites. A display window 170 on the top of the housing 110 defines a region that permits a user to observe test results as they become detectable. As described herein, "becoming detectable" specifically can relate to the accumulation of sandwich complexes at the capture site, which can be detected in various ways, such as by visual inspection of, for example, an analog or digital readout resulting from the electronic analysis of the aggregate at the capture site as further described herein. In embodiments utilizing an analog signal, a colored indicator of accumulation of labeled complexes at the test site can be visible through the display window 170. In embodiments utilizing a digital display, an electronic communication circuit an electronic communication circuit can be retained within the housing of the test device, and the electronic communication circuit can comprise a digital display whereby an analog signal can be electronically evaluated and corresponding digital signals (e.g., symbols, letters, words, and the like) can be displayed on, for example, an LCD or similar display device. Detection also can include audible signals.

Although the present disclosure is described largely in terms of direct devices/direct detection, other devices (i.e., affinity-based devices) are also intended to be encompassed herein. Affinity-based devices operate on similar principles, but rely on indirect binding (wherein one member of an affinity pair (e.g., biotin) is present on a capturable conjugate (and subsequently on any diffusible sandwich complex formed therefrom) and the other member of the affinity pair (e.g., avidin) is present on the capture medium section of the substrate).

The housing of the device of the present disclosure particularly exhibits an ergonomic structure that increases the ease of use of the test device by the test subject or user. As is more evident by the further disclosure herein and the appended drawings, the combined curvature and dimensions of the test device enable a user to more easily position the sample receiving member in a urine stream in a manner and for a duration suitable to apply the test sample to the sample receiving member in a volume useful for proper testing and without flooding of the device.

As seen in the embodiment illustrated in FIG. 1 through FIG. 5, the housing 110 is shaped and dimensioned such that the width of the housing body 130 is greater than the width of the housing handle 140. In certain embodiments, the ratio of the housing body width to the housing handle width can be about 1.1 to 1 or greater, about 1.2 to 1 or greater, or about 1.3 to 1 or greater. In further embodiments, the ratio of the housing body width to the housing handle width can be about 1.1 to about 2, about 1.15 to about 1.8, or about 1.2 to about 1.6.

The housing body 130 and the housing handle 140 can be interconnected directly or by a housing midsection 160. In specific embodiments, the housing midsection 160 has a width that is approximately equal to the width of the housing handle 140 or is less than the width of the housing handle. In some embodiments, the housing body 130, the housing handle 140, and the housing midsection 160 can have widths defined by $W_1$, $W_2$, and $W_3$, respectively, and these housing structures can have a dimensional relation such that $W_2 > W_1 > W_3$. In certain embodiments, the test device 100 can have an overall length (including the cap 120) of about 14 cm to about 21 cm, about 15 cm to about 20 cm, or about 15.5 cm to about 18 cm. The cap can have a length of about 3 cm to about 4 cm. In various embodiments, the housing handle 140 can comprise about 30% or greater, about 40% or greater, or about 50% or greater of the total length of the housing.

Figure 4:
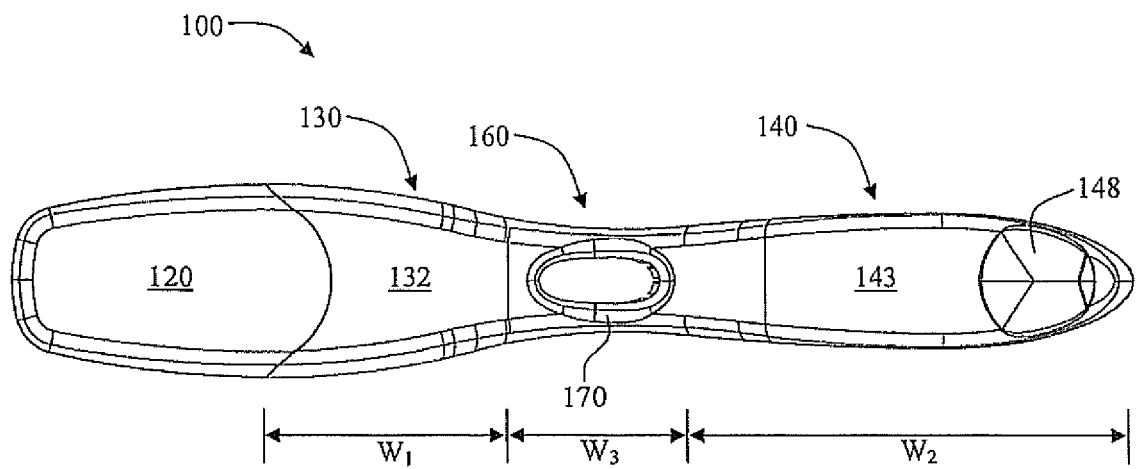
FIG. 4 is a top view of the diagnostic test device according to the example embodiment of the present disclosure.

As particularly seen in FIG. 4, the housing 110 of the test device 100 can have a multiply curved perimeter and, in some embodiments, the multiply curved perimeter can define substantially an elongated hourglass shape. The housing body 130, housing handle 140, and housing midsection 160 can each independently have a thickness of about 6 mm to about 18 mm, about 8 mm to about 16 mm, or about 10 to about 14 mm. In particular, the housing body can be defined by a curved lower surface and, in particular, by a curved lower surface 161 of the housing midsection 160 and/or a curved lower surface 144 of the housing handle 140.

The display window 170 can be positioned in the housing 110 so as be approximately centered along the length of the housing. In specific embodiments, the display window 170 can be positioned in the housing midsection. In embodiments utilizing an analog display, the display window preferably is located in a portion of the housing corresponding to the test site on the test member, as discussed in greater detail below. In embodiments utilizing a digital display, the display window can be located at a variety of positions on the housing.

The housing handle in particular can be adapted for ease of use and ease of positioning the device for midstream application of a test sample. The housing handle can be adapted to provide a user with increased comfort of handling, improved grip on the device, and improved sanitary handling during and after sample application. The housing handle further can cooperate with one or more additional elements of the test device to provide desirable positioning of the test device on a resting surface, such as a table or counter top.

Figure 3:
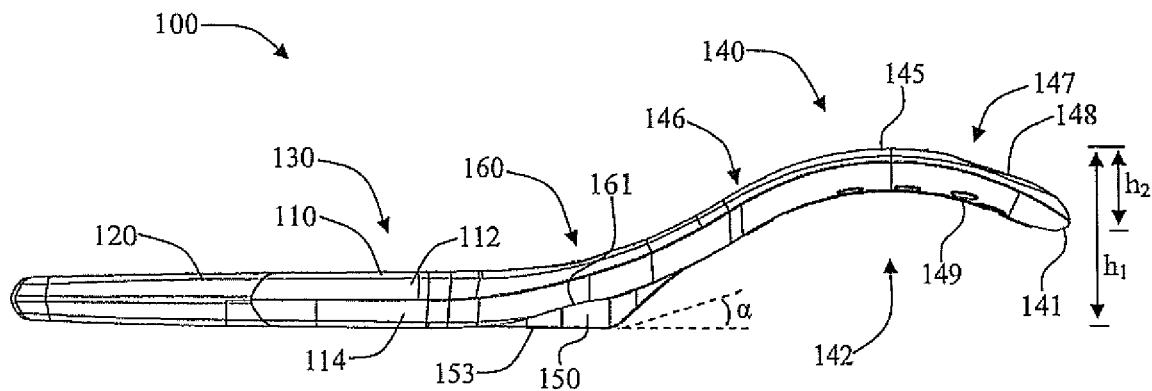
FIG. 3 is a side view of the diagnostic test device according to the example embodiment of the present disclosure.

Referring to the embodiment of FIG. 3 in particular, the housing handle 140 of the test device 100 can be characterized by a curving handle arch 142 rising up from the substantially flat housing body 130 to a maximum height relative to the housing body and then turning downward. In particular, the handle arch 142 can be defined by an apex at a transverse section 145 of the housing handle that interconnects a handle ascending section 146 and a handle descending section 147. In some embodiments, the apex of the transverse section can define the maximum height of the curved housing handle relative to the housing body 130. The handle descending section 147 ends at a handle terminus 141, which can define the rearward end of the test device 100.

The housing handle arch 142 can be defined by a total height as well as a partial height. The total height $h_1$ can be defined by a distance between the upper surface 143 of the housing handle 140 at the apex of the handle transverse section 145 and the lower surface 131 of the housing body 130. In some embodiments, such height can be about 15 mm or greater, about 20 mm or greater, or about 25 mm or greater. In further embodiments, $h_1$ can be about 15 mm to about 40 mm, about 20 mm to about 36, or about 22 mm to about 32. The partial height $h_2$ can be defined by a distance between the top of the housing handle 140 at the apex of the handle transverse section 145 and the bottom of the handle terminus 141. Preferably, $h_2$ can be defined by the formula $h_1 > h_2 > T_{handle}$, wherein $T_{handle}$ is the thickness of the housing handle 140.

Figure 2:
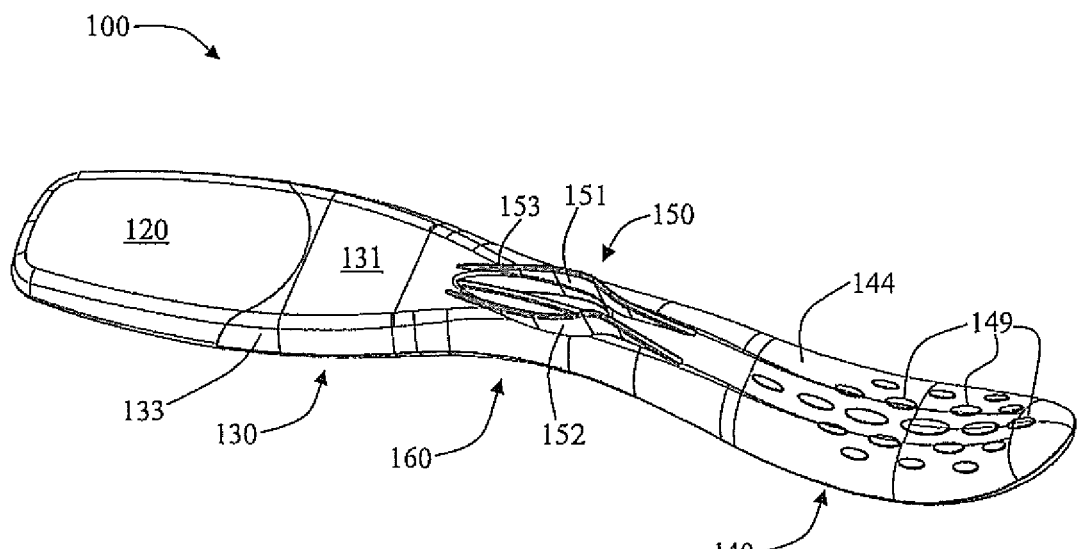
FIG. 2 is a bottom perspective view of the diagnostic test device according to the example embodiment of the present disclosure more particularly showing a base member of the device and textures present on a handle of the device.
Figure 5:
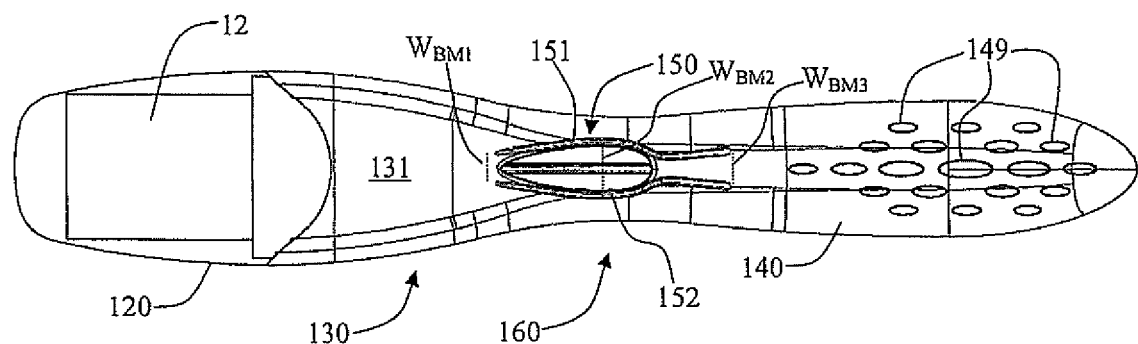
FIG. 5 is a bottom view of the diagnostic test device according to the example embodiment of the present disclosure.

The housing handle 140 further can be defined by one or more elements adapted to improve a user's grip on the test device 100. For example, in some embodiments, a concavity 148 (e.g., a recess or indentation) can be present, particularly on the upper surface 143 of the housing handle 140 on the handle descending section 147. The concavity may be characterized as being a handle grip recess or a thumb grip and may be substantially dimensioned for receiving the curved surface of a user's thumb or finger. As another example, the housing handle 140 can include one or more handle grip textures 149 or similar elements that function to substantially prevent slipping of the handle in the hand or fingers of a user. As illustrated in FIG. 2 and FIG. 5 in particular the handle grip textures 149 can comprise raised members (although recessed members also are encompassed) that provide a break in the substantially smooth texture of the remaining surface of the test device 100. Preferably, the handle grip textures 149 can be adapted to provide friction such that the coefficient of friction between human skin and the handle grip texture 149 exceeds the coefficient of friction between human skin and the remaining surface of the test device 100. For example, the handle grip textures 149 can comprise rubber or a further elastomeric material that provides substantially a non-slip texture. Similarly, a raised and/or roughened surface may be utilized to form a sufficient grit and provide substantially a non-slip texture. Referring to the figures, the handle grip textures 149 are illustrated on only the lower surface 144 of the housing handle 140; however, it is understood that textures also or alternatively may be present at other locations on the housing handle.

Referring to FIG. 3 in particular, the housing 110 of the test device 100 can be defined as comprising a housing handle 140 that lies substantially or completely in a horizontal plane that is above the horizontal plane of the housing body 130. As such, when placed on a flat surface (e.g., a table top or counter top), the housing body 130 may be substantially or completely in contact with the surface while the housing handle 140 is not in physical contact with the surface. In particular, the housing handle 140 can be positioned entirely above the lower surface 131 of the housing body 130. Accordingly, the test device 100 may be defined in relation to its center of gravity and/or the relative weights of the separately defined sections of the housing 110. Preferably, the center of gravity of the test device 100 can be substantially at the section of the housing including the display window 170. In some embodiments, the center of gravity of the housing may be substantially in the housing midsection 160. The center of gravity specifically may reside at a point along the length of the test device 100 (measured from the front of the cap 120 to the handle terminus 141) that is greater than 50% of the total length of the test device. In such embodiments, the relative weights of the housing body 130 and the housing handle 140 may be such that the test device 100 remains upright when placed in an upward facing position on a flat surface. Such orientation may be maintained in the presence of the cap 120 as well as in the absence of the cap.

In some embodiments, the test device may be defined by a base member 150 that is connected to a lower surface of the housing 110. The base member 150 may be removably attached to the housing 110. Alternatively, the base member 150 may be monolithically formed with the housing 110, particularly with the housing midsection 160. In some embodiments, the base member 150 effectively extends the overall length of the lower surface 131 of the housing body 130. The base member 150 can be positioned substantially below the position of the display window 170. The base member 150 likewise can be positioned substantially at a position along the length of the test device 100 corresponding to the center of gravity of the test device, as discussed above.

In certain embodiments, the housing midsection 160 can be curved so as to transition the housing between the substantially flat orientation of the housing body 130 and the arching orientation of the housing handle 140, particularly with the handle ascending section 146. As such, all or part of the housing midsection 160 may lie in a horizontal plane above the horizontal plane of the flat housing body 130. In other words, when the flat, lower surface 131 of the housing body 130 is resting on a flat surface, part or all of the housing midsection 160 may be positioned above the flat surface. In specific embodiments, the base member can be in contact with one or more of the housing body 130, the housing midsection 160, and the housing handle 140. In particular, the base member may extend from the lower surface 131 of the housing body 130 and increase in height moving rearward. As seen in FIG. 3, the base member 150 can comprise a horizontal support surface 153 that is collinear with the lower surface 131 of the housing body 130 and that extends rearward from the lower surface of the housing body. The base member 150 thus can be defined as having a height or thickness that tapers moving forward and transitions into the lower surface 131 of the housing body 130. The horizontal support surface 153 of the base member 150 forms an angle α with the curved lower surface of the housing. In the illustrated embodiment, the curved lower surface is the curved lower surface 161 of the housing midsection 160; however, the curved lower surface alternatively may be a curved lower surface of the housing body and/or the housing handle. In various embodiments, the angle α can be about 5° or greater, about 10° or greater, or about 15° or greater. In particular, the angle α can be about 5° to about 45°, about 10° to about 40°, or about 15° to about 35°. The base member 150 thus can be characterized as facilitating a stable, flat positioning of the test device 100 on a flat surface. In certain embodiments, the horizontal support surface 153 of the base member 150 can have a length of about 10 mm or greater or about 15 mm or greater. In particular, the horizontal support surface can have a length of about 10 mm to about 30 mm or about 15 mm to about 25 mm. In specific embodiments, the horizontal support surface 153 of the base member 150 can effectively increase the support length of lower surface 131 of the housing body 130. The support length can define the length along the housing 110 that is in contact with a support surface when resting in an upward facing position. In particular, the horizontal support surface 153 of the base member 150 can effectively increase the support length of lower surface 131 of the housing body 130 about 5% or greater, about 10% or greater, or about 20% or greater.

The base member 150 can be a single, unitary member. As seen in the illustrated embodiments, the base member 150 can be formed collectively of a first base member wall 151 and a second base member wall 152. As seen particularly in FIG. 5, the respective walls (151, 152) of the base member 150 can be curved. Specifically, referencing the outer surfaces, the first base member wall 151 and the second base member wall 152 each comprise a convex curve in the forward sections thereof and a concave curve in the rearward sections thereof. As such, the width $W_{BM1}$ of the front most section of the base member 150, the width $W_{BM2}$ of the central section of the base member, and the width $W_{BM3}$ of the rear most section of the base member can have the following relationship: $W_{BM1} < W_{BM2} > W_{BM3}$.

In addition to facilitating a stable, upward facing positioning of the test device 100 on a flat surface, the base member 150 beneficially facilitates an alternate positioning of the test device that can increase the viewing comfort of a user in a seated position if desired. In particular, the test device 100 can be positioned on either side on a flat surface so as to rest at an angle relative to the surface that is greater than 0° and less than 90°. For example, the angle relative to the surface can be about 10° to about 85°, about 20° to about 80°, or about 30° to about 75°. In particular embodiments, such position can be achieved through substantially a three point contact with the flat surface. For example, in the angled resting position, surface contact can be made with a wall (151 or 152) of the base member 150, a side wall of the housing body 130, and a side wall of the housing handle (e.g., the handle descending section 147). In particular, the portion of the wall of the base in contact with the flat surface can be a portion of the convex curved forward section. In some embodiments, to increase the stability of this angled positioning of the test device, the housing body 130 can comprise angled sidewalls. In particular, referring to FIG. 1 and FIG. 2, the housing body 130 can comprise a lower body side wall 133 rising upward from the lower surface 131 of the housing body and can comprise an upper body side wall 134 extending downward from the upper surface 132 of the housing body. Specifically, the upper body side wall 134 can comprise an angle relative to the upper surface 132 of the housing body 130 that is greater than 0° and less than 90°—e.g., about 40° to about 50°. Likewise, the lower body side wall 133 can comprise an angle relative to the lower surface 131 of the housing body 130 that is greater than 0° and less than 90°—e.g., about 40° to about 50°. As such, the two angled side walls (133, 134) can meet at a point at about the midline of the housing body 130. In the angled resting position, one of the three resting points of the test device on the flat surface can comprise a point on the lower body side wall 134.

The test device according to the present disclosure can be particularly defined by the curvatures of the surfaces of the device housing. The nature of the curvatures are further illustrated in FIG. 10 through FIG. 25 (wherein like numbers refer to like elements as described in reference to FIG. 1 through FIG. 5).

The housing 110 of the test device 100 encloses the components necessary for carrying out an assay, such as a lateral flow test member.

Figures 6, 7:
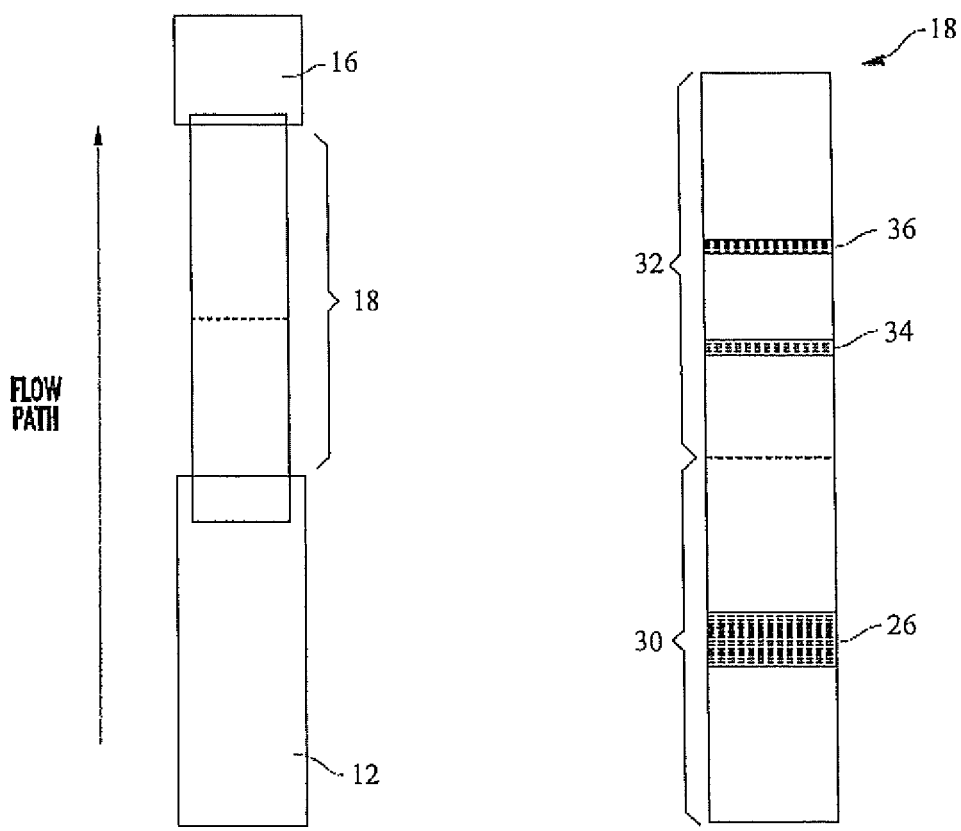
FIG. 6 is a top view of lateral flow test components according to an exemplary embodiment of the present disclosure comprising a reservoir absorbent material, a biphasic substrate, and a sample receiving member outside of a housing.
FIG. 7 is a top view of a biphasic substrate for use in a diagnostic test device according to an exemplary embodiment of the disclosure.

FIG. 6 shows an example of lateral flow test components that can be present in a test device according to the present disclosure. These test components can comprise a sample receiving member 12, biphasic chromatographic substrate 18, and reservoir absorbent material 16. When the device is placed in contact with a fluid sample, the fluid is transported by capillary action, wicking, or simple wetting along the flow path downstream through sample receiving member 12, along chromatographic substrate 18, and into reservoir absorbent material 16, generally as depicted by the arrow. Sample receiving member 12 may also serve as a filter which can remove particulate matter and interfering factors from a sample. The sample receiving member 12 preferably is a bibulous hydrophilic material which facilitates absorption and transport of a fluid sample to the biphasic chromatographic substrate 18. Such materials may include cellulose acetate, hydrophilic polyester, or other materials having similar properties. A combination of absorbent materials also may be used. As noted above, a filtration means which limits the introduction to the test site of contaminants from the sample may also be included. In certain embodiments, the sample receiving member 12 can be omitted, and the release medium of a biphasic substrate 18 can itself act as the sample receiving member. Such embodiments of the assay materials are useful in performing dipstick assays. By providing a reservoir of sorbent material (e.g., absorbent paper made from cotton long linter fibers or cellulosic materials) disposed beyond the chromatographic substrate, a relatively large volume of the test fluid and any analyte it contains can be drawn through the test area to facilitate background clearance and thereby aid sensitivity. The reservoir absorbent generally facilitates capillary action along the chromatographic substrate and absorbs excess fluid contained within the device.

FIG. 7 illustrates in greater detail an exemplary biphasic chromatographic substrate 18, comprising a release medium 30 and a capture medium 32 joined together to form a single fluid path. A band 26 of labeled binding member, e.g., an antibody-metal sol, can be releasably disposed on the release medium 30. In one embodiment, the labeled binding member is in dehydrated form. As the fluid sample moves past the band 26, the labeled binding member becomes entrained in the fluid, reconstituted (in the case of a dehydrated binding member), and binds with a particular analyte or analytes of interest present in the fluid sample. Accordingly, the resulting complex comprising a binding antibody, a label component, and an analyte for identification (e.g., hCG) advances along with the sample front until it reaches the capture site 34. In this particular embodiment, the capture site includes at least one immobilized capture antibody which binds to a different epitope of the analyte. Accordingly, a sandwich complex including the desired analyte is formed at the capture site 34. If desired, a control site 36 can be present. In further embodiments, indirect binding, such as otherwise described herein, may be used.

Figure 8:
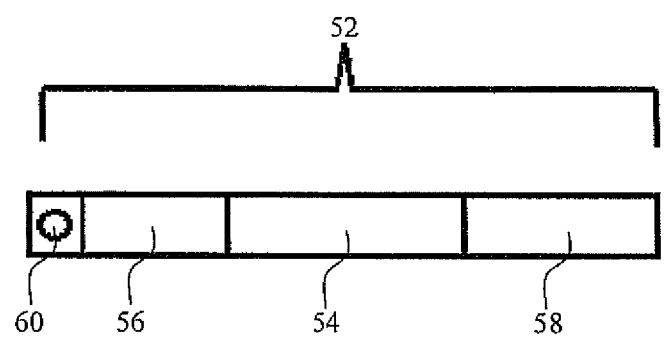
FIG. 8 is a top view of a lateral flow test strip comprising a triphasic substrate according to an exemplary embodiment of the present disclosure.
Figure 9:
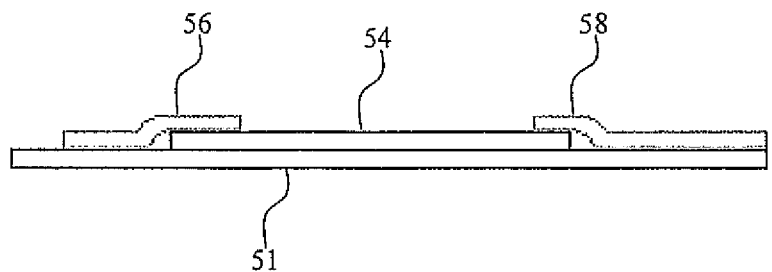
FIG. 9 is a side view of the triphasic substrate of FIG. 8
Figure 10:
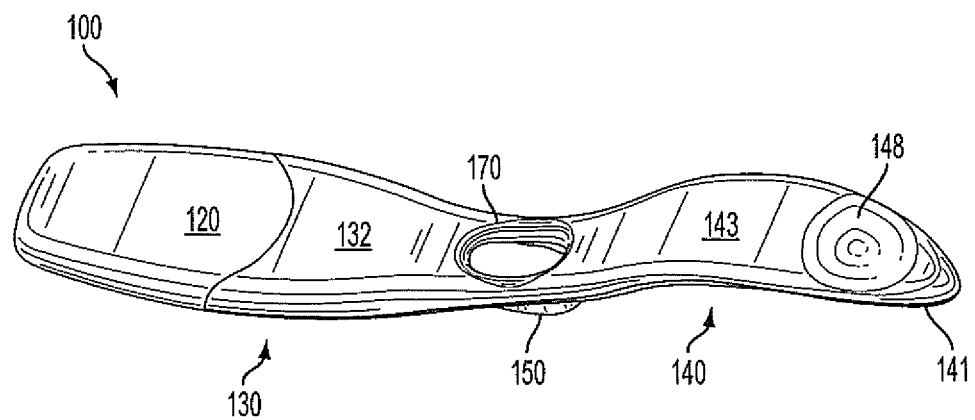
FIG. 10 is top perspective view of a diagnostic test device according to an example embodiment of the present disclosure illustrating the curvatures thereof.
Figure 11:
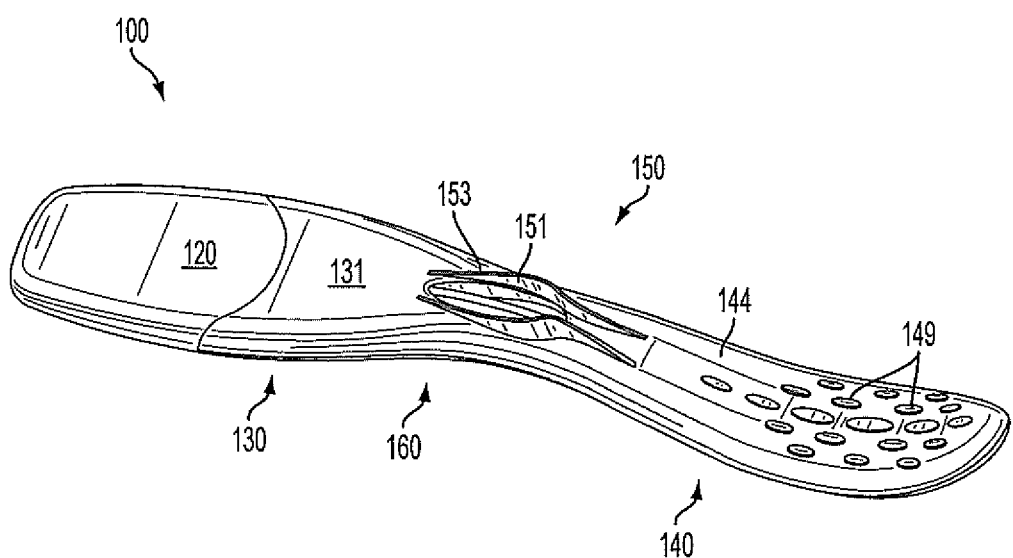
FIG. 11 is bottom perspective view of the diagnostic test device of FIG. 10.
Figure 12:
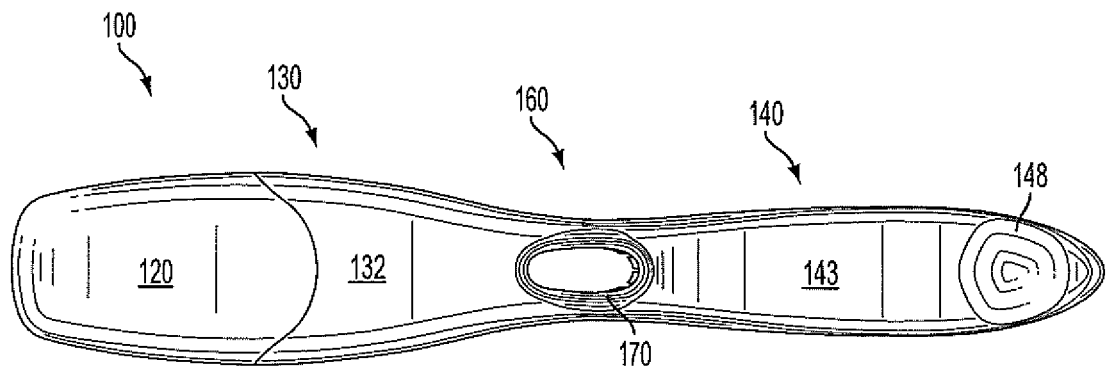
FIG. 12 is a top plan view of the diagnostic test device of FIG. 10.
Figure 13:
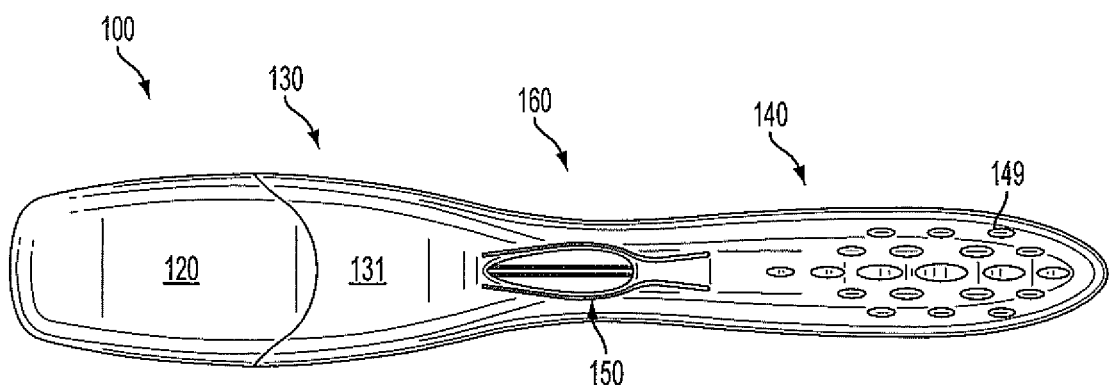
FIG. 13 is a bottom plan view of the diagnostic test device of FIG. 10.
Figure 14:
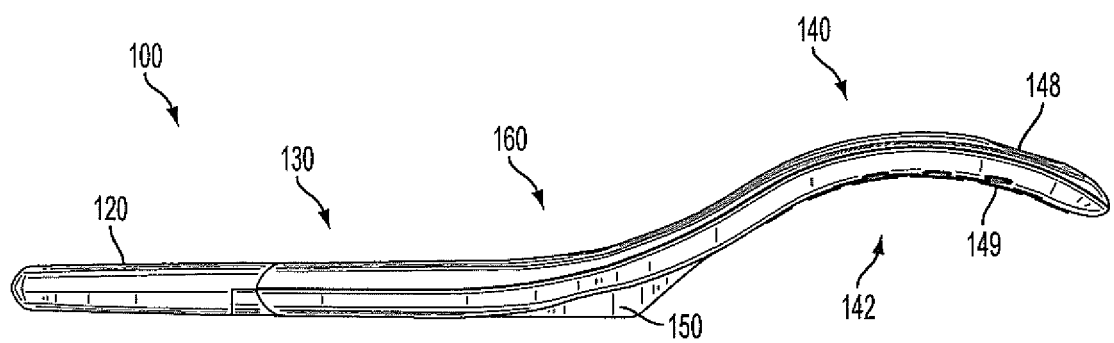
FIG. 14 is a side view of the diagnostic test device of FIG. 10.
Figure 15:
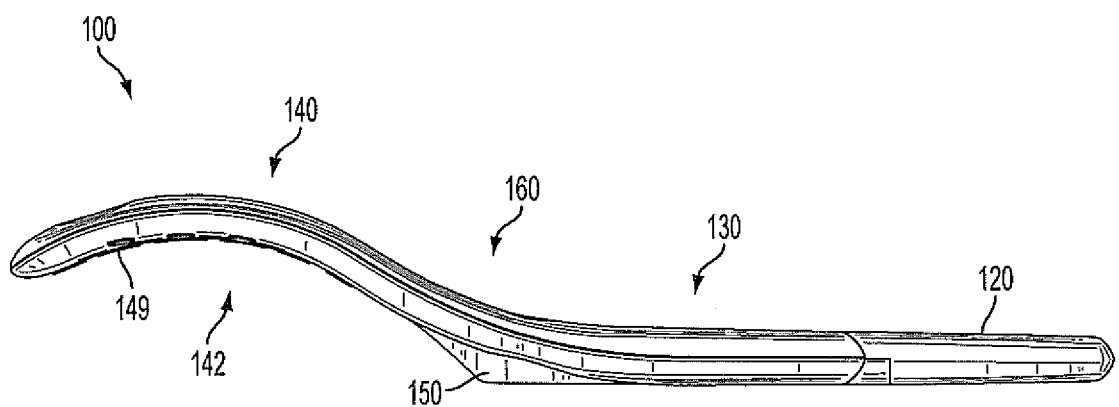
FIG. 15 is an opposite side view of the diagnostic test device of FIG. 10.
Figure 16:
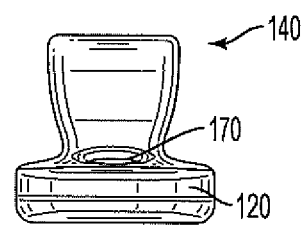
FIG. 16 is a front end view of the diagnostic test device of FIG. 10.
Figure 17:
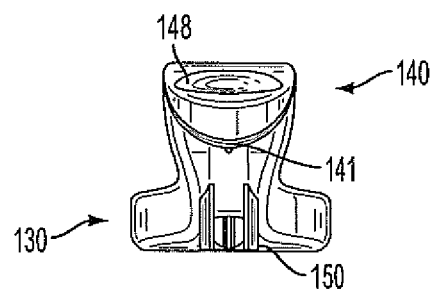
FIG. 17 is a rear end view of the diagnostic test device of FIG. 10.
Figure 18:
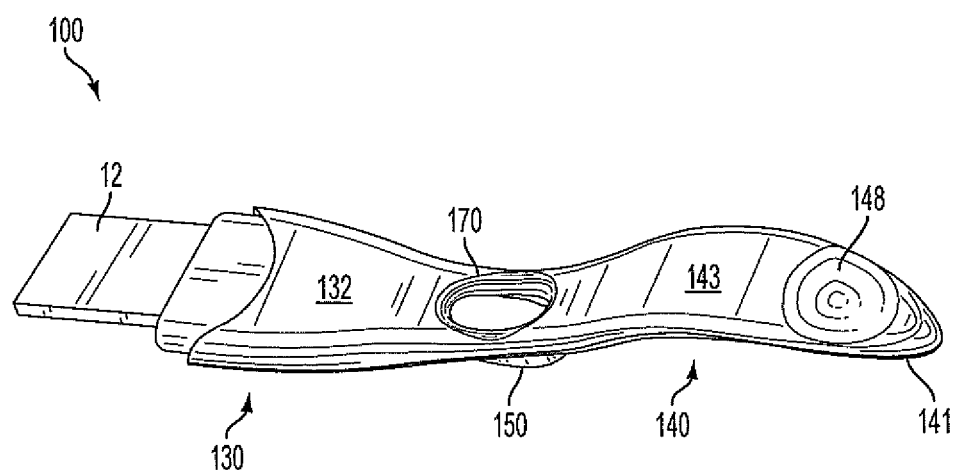
FIG. 18 is top perspective view of the diagnostic test device of FIG. 10 without the front end cap.
Figure 19:
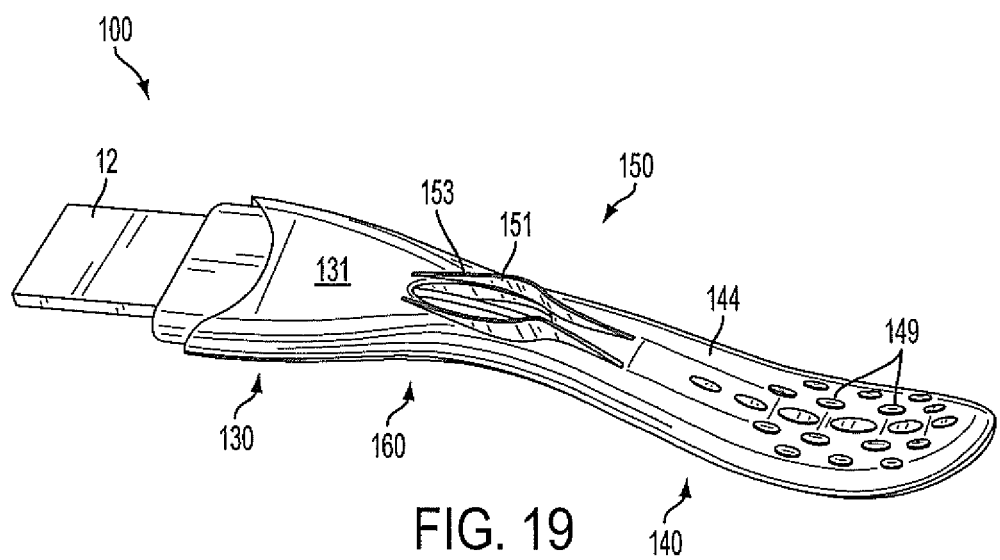
FIG. 19 is a bottom perspective view of the diagnostic test device of FIG. 18.
Figure 20:
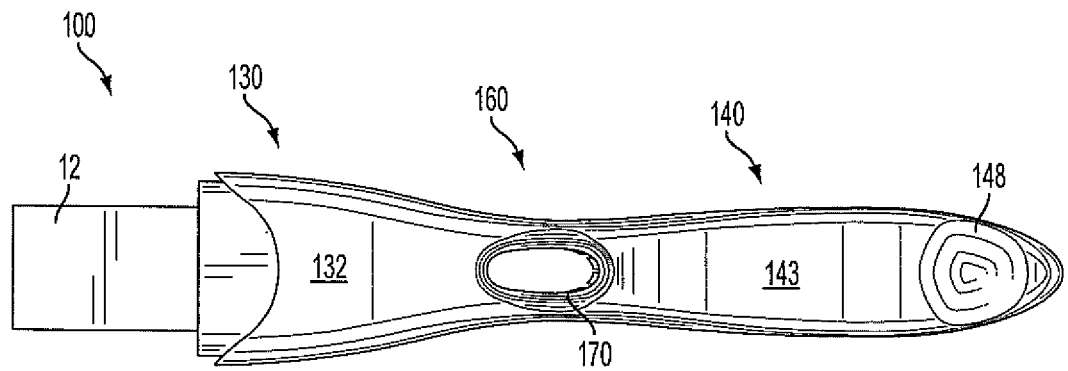
FIG. 20 is a top plan view of the diagnostic test device of FIG. 18.
Figure 21:
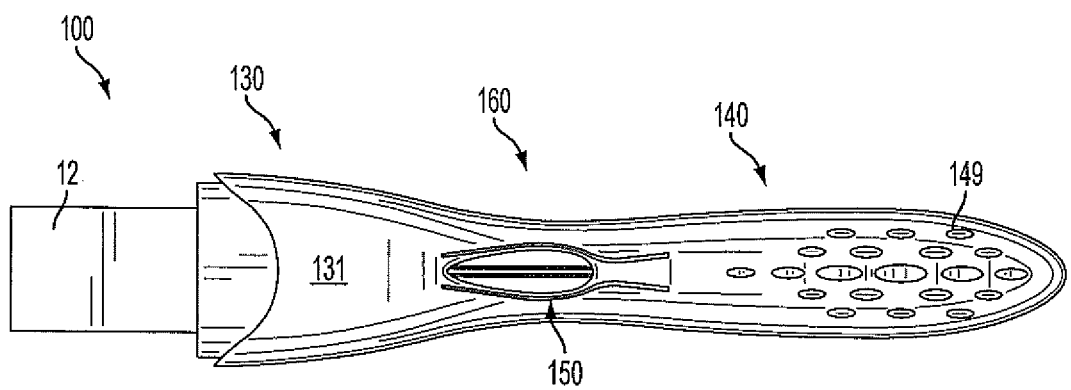
FIG. 21 is a bottom plan view of the diagnostic test device of FIG. 18.
Figure 22:
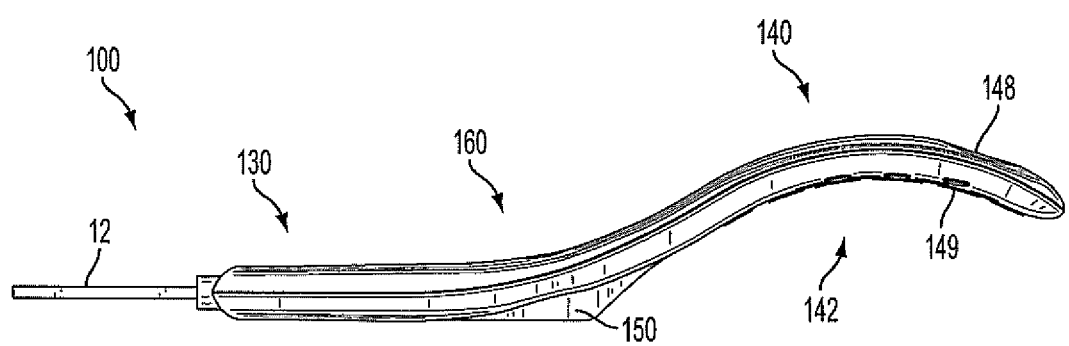
FIG. 22 is a side view of the diagnostic test device of FIG. 18.
Figure 23:
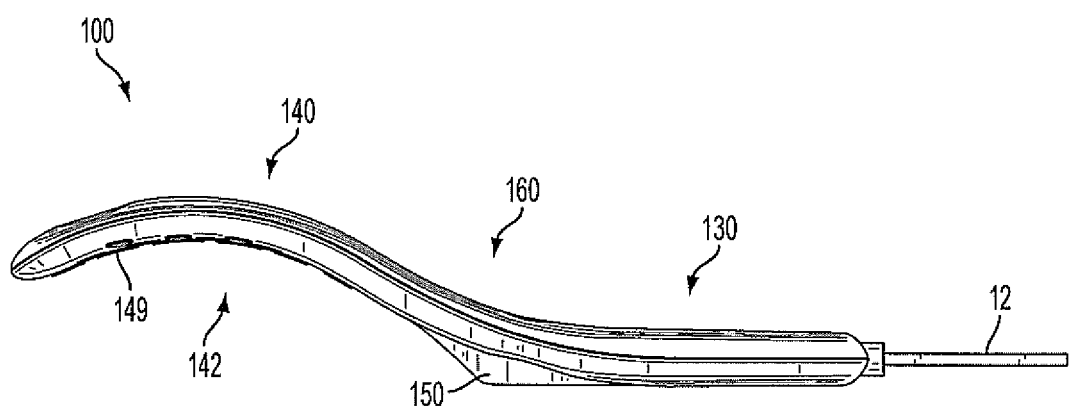
FIG. 23 is an opposite side view of the diagnostic test device of FIG. 18.
Figure 24:
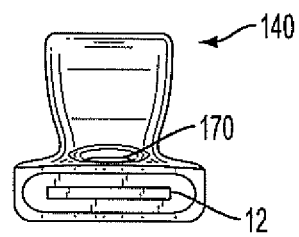
FIG. 24 is a front end view of the diagnostic test device of FIG. 18.
Figure 25:
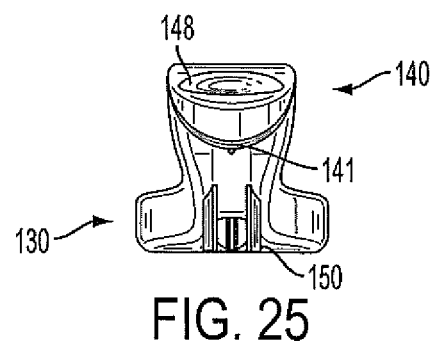
FIG. 25 is a rear end view of the diagnostic test device of FIG. 18.

A further exemplary lateral flow test strip that can be present in a device according to the present disclosure is illustrated in FIG. 8. In particular, a triphasic test strip 52 is shown and is formed of a release medium 58, a capture medium 54, and a reservoir 56. An alignment hole 60 is shown and can be used to align the test strip within a casing by mating with an appropriately positioned pin. FIG. 9 illustrates an overlapping relation of the release medium 58, capture medium 54, and reservoir 56. Although not illustrated, the release medium 58 can be in fluid communication with a sample receiving member as already described herein (e.g., element 12 in FIG. 6). Further, the release medium 58, capture medium 54, and reservoir 56 can be laminated onto a backing 51, which can be, for example, an opaque plastic film or sheet. In use, the appropriate antibodies, binding members, and labels can be positioned on the release medium 58 and the capture medium 54, and an advancing fluid sample can cause formation of a complex, such as, for example, the combination of a binding antibody, a label component, and an analyte for identification. This complex then can bind with a binding member on the capture medium 54. The resulting, bound complex can be analyzed by the detection means as otherwise discussed herein, and a result then can be provided via a digital display, for example, an LCD, visible through the display window 170. The release and capture media can be constructed of materials as described above in relation to a biphasic substrate embodiment.

For further detail regarding various testing devices, methods of use, and parameters thereof, see for example U.S. Pat. Nos. 5,739,041; 6,046,057; 6,277,650; 6,319,676; 6,767,714; 7,045,342, 7,763,454; 7,776,618 and 8,211,711 to Nazareth et al., and U.S. Patent Application Publication Nos. 2002/0042082, 2004/0171174; 2008/0213920; 2010/0051350; 2010/0239460; 2010/0240149; 2010/0261293; 2010/0267166; and 2011/0201122 to Nazareth et al., and 2012/0083044 to Sturman et al.; which are incorporated herein by reference in their entireties.

In further embodiments, the present disclosure provides various methods for detecting the presence of an analyte (such as hCG) in a fluid sample. For example, a method according to the present disclosure can comprise adding a fluid sample to a first portion of a presently disclosed test device, allowing the sample to flow across a substrate in the test device (e.g., a biphasic or triphasic substrate), and determining the presence of the analyte in the liquid sample by inspection of a signal visible through the display window.

EXPERIMENTAL

Test devices according to the present disclosure were evaluated through flood testing to evaluate liquid uptake and overall time to assay results. Referring to Table 1, flood testing evaluated the effects of tap versus dip application of the test sample. A series of devices according to the present disclosure were held in a stream of water at a high flow rate (70-80 mL/sec) for 15 seconds while a parallel series of devices were dipped in water for 5 seconds as the control devices. By comparing the change in weight of the devices, the amount of liquid was calculated to determine if flooding (i.e., detrimentally excess uptake of liquid) had occurred. Further, the development of a control line within the chromatographic assay was considered for demonstration of proper immunoassay progression.

TABLE 1

|  | High Flow Tap Testing | | Dip Testing | |
| --- | --- | --- | --- | --- |
| Replicates | Δ Weight (g) | Functionality | Δ Weight (g) | Functionality |
| 1 | 1.33 | Control Line Present | 1.26 | Control Line Present |
| 2 | 1.30 | Control Line Present | 1.22 | Control Line Present |
| 3 | 1.33 | Control Line Present | 1.29 | Control Line Present |
| 4 | 1.31 | Control Line Present | 1.22 | Control Line Present |
| 5 | 1.37 | Control Line Present | 1.23 | Control Line Present |
| 6 | 1.25 | Control Line Present | 1.21 | Control Line Present |

TABLE 1-continued

|   | High Flow Tap Testing | | Dip Testing | |
|---|---|---|---|---|
| Replicates | Δ Weight (g) | Functionality | Δ Weight (g) | Functionality |
| 7 | 1.32 | Control Line Present | 1.25 | Control Line Present |
| 8 | 1.27 | Control Line Present | 1.26 | Control Line Present |
| 9 | 1.27 | Control Line Present | 1.25 | Control Line Present |
| 10 | 1.28 | Control Line Present | 1.32 | Control Line Present |
| AVG | 1.30 | All Devices Function | 1.25 | All Devices Function |

Referring to Table 2, devices according to the present disclosure also were tested for completion times in multiple reading orientations as compared to known devices. Development of test lines occurred with each tested device, and the completion times are shown in Table 2.

TABLE 2

| Replicates | Present Devices Traditional Read | Present Devices Comfort Read | Control Device Traditional Read |
|---|---|---|---|
| 1 | 30 sec | 31 sec | 31 sec |
| 2 | 29 sec | 29 sec | 34 sec |
| 3 | 30 sec | 32 sec | 32 sec |
| 4 | 31 sec | 29 sec | 35 sec |
| 5 | 29 sec | 30 sec | 32 sec |
| AVG | 29.8 sec | 30.2 sec | 32.8 sec |

Many modifications and other embodiments of the disclosure set forth herein will come to mind to one skilled in the art to which these disclosures pertain having the benefit of the teachings presented in the foregoing descriptions. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A diagnostic test device comprising:
a housing body having a lateral flow test component positioned therein, the housing body being in a horizontal plane; and
a substantially arch shaped handle interconnected with the housing body, the handle being positioned above the horizontal plane of the housing body;
wherein the lateral flow test component comprises a sample receiving member extending outward from the housing body at a forward end thereof.

2. The diagnostic test device according to claim 1, further comprising a base member attached to a lower surface of the housing body.

3. The diagnostic test device according to claim 2, wherein the base member comprises a horizontal support surface.

4. The diagnostic test device according to claim 3, wherein the horizontal support surface is substantially collinear with a lower surface of the housing body.

5. The diagnostic test device according to claim 4, wherein the base member extends rearward from the lower surface of the housing body and increases in height moving rearward.

6. The diagnostic test device according to claim 5, wherein the horizontal support surface of the base member effectively increases a support length of the lower surface of the housing body by about 5% or greater.

7. The diagnostic test device according to claim 3, wherein the horizontal support surface of the base member forms and angle α with the lower surface of the housing body.

8. The diagnostic test device according to claim 7, wherein the angle a is about 5° or greater.

9. The diagnostic test device according to claim 3, wherein the horizontal support surface of the base member has a length of about 10 mm or greater.

10. The diagnostic test device according to claim 3, wherein the horizontal support surface of, the base member has a length of about 10 mm to about 30 mm.

11. The diagnostic test device according to claim 2, wherein the base member is monolithically formed with the housing body.

12. The diagnostic test device according to claim 2 wherein the base member its a single, unitary member.

13. The diagnostic test device according to claim 2, wherein the base member is defined by a first base member wall and a second base member wall.

14. The diagnostic test device according to claim 13, wherein the base member walls are curved.

15. The diagnostic test device according to claim 14, wherein the curved base member walls are defined by a forward section and a rearward section, and wherein the curved base member walls each comprise a convex curve in the forward sections thereof and a concave curve in the rearward sections thereof with respect to outer surfaces of the walls.

16. The diagnostic test device according to claim 15, wherein the curved base member walls define a width $W_{BM1}$ at the forward section thereof, a width $W_{BM2}$ at a central section thereof, and a width $W_{BM3}$ at the rearward section thereof, and wherein the respective widths are defined by the formula $W_{BM1} < W_{BM2} > W_{BM3}$.

17. The diagnostic test device according to claim 1, wherein the housing body is defined by a lower housing body and an upper housing body.

18. The diagnostic test device according to claim 17, wherein the lower housing body comprises a sidewall that is defined by an angle relative to a lower surface of the lower housing body, the angle being greater than 0° and less than 90°.

19. The diagnostic test device according to claim 17, wherein the upper housing body comprises a sidewall that is defined by an angle relative to an upper surface of the upper housing body, the angle being greater than 0° and less than 90°.

20. The diagnostic test device according to claim 1, wherein the substantially arch shaped handle is defined by an ascending section, a transverse section, and a descending section.

21. The diagnostic test device according to claim 20, wherein the handle is defined by a total height $h_1$ that is a distance between an apex of an upper surface of the transverse section of the handle and a lower surface of the housing body, the height $h_1$ being about 15 mm or greater.

22. The diagnostic test device according to claim 21, wherein the height $h_t$ is about 15 mm to about 40 mm.

23. The diagnostic test device according to claim 22, wherein the handle has a thickness $T_{handle}$, wherein the handle is defined by a partial height $h_2$ that is a distance between the apex of the upper surface of the transverse section of the handle and a bottom of a terminus of the handle, and wherein $h_2$ is defined by the formula $h_1 > h_2 > T_{handle}$.

24. The diagnostic test device according to claim 20, wherein the substantially arch shaped handle comprises a concavity on an upper surface thereof.

25. The diagnostic test device according to claim 20, wherein substantially arch shaped handle comprises textures on a lower surface thereof.

26. The diagnostic test device according to claim 25, wherein the textures are defined by a plurality of raised members.

27. The diagnostic test device according to claim 25, wherein the textures comprise rubber or a further elastomeric material.

28. The diagnostic test device according to claim 1, wherein the substantially arch shaped handle comprises about 40% or greater of the total length of the device.

29. The diagnostic test device according to claim 1, wherein the device further comprises a housing midsection interconnecting the housing body and the housing handle.

30. The diagnostic test device according to claim 1, wherein the housing body further comprises a display window.

31. The diagnostic test device according to claim 1, wherein the device further comprises a cap that removably engages the housing body.

32. The diagnostic, test device according to, claim 1, wherein the sample receiving member has a surface area of about 15 cm² or greater.

33. The diagnostic test device according to claim 1, wherein the sample receiving member has a surface area of about 15 cm² to about 25 cm².

34. The diagnostic test device according to claim 1, wherein the sample receiving member is defined by a thickness of about 1.5 mm to about 2.4 mm, a width of about 16 mm to about 20 mm, and a length of about 45 mm to about 55 mm.

35. The diagnostic test device according to claim 1, wherein the lateral flow test component comprises a biphasic substrate.

36. The diagnostic test device according to claim 1, wherein the lateral flow test component comprises a triphasic substrate.

37. The diagnostic test device according to claim 1, wherein the lateral flow test component comprises a release medium in fluid communication with a capture medium.

38. The diagnostic test device according to claim 37, wherein the release medium comprises one or more releasably attached antibodies that are reactive with an analyte.

39. A diagnostic test device comprising:
a housing body having a lateral flow test component positioned therein, the housing body being in a horizontal plane; and
a substantially arch shaped handle interconnected with the housing body, the handle being positioned above the horizontal plane of the housing body;
wherein the substantially arch shaped handle comprises about 30% or greater of the total length of the device.

40. A diagnostic test device comprising;
a housing body having a lateral flow test component positioned therein, the housing body being in a horizontal plane; and
a substantially arch shaped handle interconnected with the housing body, the handle being positioned above the horizontal plane of the housing body;
wherein the substantially arch shaped handle is defined by an ascending section, a transverse section, and a descending section; and
wherein the substantially arch shaped handle comprises a concavity on an upper surface of the descending section of the handle.

41. A diagnostic test device comprising:
a housing body having a lateral flow test component positioned therein, the housing body being in a horizontal plane;
a substantially arch shaped handle interconnected with the housing body, the handle being positioned above the horizontal plane; and
a base member attached to a lower surface of the housing body, wherein the base member comprises a horizontal support surface that forms an angle α with the lower surface of the housing body, said a being about 5° to 45°.

* * * * *